United States Patent [19]

Fuso et al.

[11] Patent Number: 5,312,917
[45] Date of Patent: May 17, 1994

[54] WATER-SOLUBLE TRIAZINE DERIVATIVES

[75] Inventors: Francesco Fuso, Therwil; Gerhard Reinert, Allschwil, both of Switzerland

[73] Assignee: Ciba-Geigy Corporation, Ardsley, N.Y.

[21] Appl. No.: 987,875

[22] Filed: Dec. 9, 1992

[30] Foreign Application Priority Data

Sep. 12, 1991 [CH] Switzerland ............... 3609/91

[51] Int. Cl.$^5$ ............................................. C07D 401/12
[52] U.S. Cl. ................................. 544/198; 544/207; 544/209; 544/212; 544/113
[58] Field of Search ............... 544/113, 212, 207, 209, 544/198

[56] References Cited

U.S. PATENT DOCUMENTS

| 4,189,570 | 2/1980 | Bonometti et al. | 544/211 |
|---|---|---|---|
| 4,189,576 | 2/1980 | Alterfer et al. | 544/211 |
| 4,361,698 | 11/1982 | Olten et al. | 544/211 |
| 4,530,950 | 7/1985 | Raspani et al. | 524/100 |
| 4,740,597 | 4/1988 | Franke et al. | 544/211 |
| 4,771,129 | 9/1988 | Kawashita et al. | 534/803 |
| 4,839,468 | 6/1989 | Nickel et al. | 534/604 |

FOREIGN PATENT DOCUMENTS

| 036133 | 9/1981 | European Pat. Off. . |
|---|---|---|
| 062825 | 10/1982 | European Pat. Off. . |
| 172790 | 2/1986 | European Pat. Off. . |
| 1948859 | 9/1986 | European Pat. Off. . |
| 453405 | 10/1991 | European Pat. Off. . |
| 3740650 | 6/1989 | Fed. Rep. of Germany . |
| 2367755 | 10/1977 | France . |
| 2368479 | 10/1977 | France . |
| 2521143 | of 1983 | France . |

OTHER PUBLICATIONS

Korolev et al. Chem. Abst. vol. 105:116416f (1986).
Takimoto et al Chem. Abst, vol. 115:73798u (1991).

Primary Examiner—John M. Ford
Attorney, Agent, or Firm—Marla J. Mathias; George R. Dohmann

[57] ABSTRACT

Water-soluble triazine derivatives of formula (1) are disclosed. The novel compounds are representatives of sterically hindered amines (HALS stabilisers) and are suitable for enhancing the thermal and photochemical stability of undyed and dyed polyamide fibre materials.

8 Claims, No Drawings

WATER-SOLUBLE TRIAZINE DERIVATIVES

The present invention relates to water-soluble triazine derivatives, to the preparation thereof and to a process for photochemically and thermally stabilising polyamide fabrics with these compounds.

The novel compounds have the formula

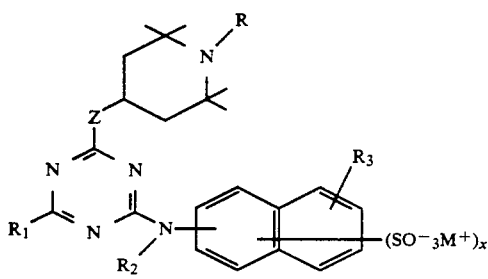

wherein

R is hydrogen, oxyl; hydroxy; $C_1$–$C_5$alkyl; $C_3$–$C_5$alkenyl; $C_1$–$C_5$alkoxy; acyl; or benzyl, $R_1$ is halogen; $C_1$–$C_5$alkyl; amino; $C_1$–$C_5$alkoxy; $C_3$–$C_5$alkenyloxy; cycloalkoxy; unsubstituted phenoxy or phenoxy which is substituted in the phenyl moiety by halogen, $C_1$–$C_5$alkyl, $C_1$–$C_5$alkoxy, carboxy, carboxy-$C_1$–$C_5$alkyl, carbamoyl, mono- or di-$C_1$–$C_5$-acylamino or acyl; phenyl; phenyl-$C_1$–$C_5$alkyl; phenylthio; phenyl-$C_1$–$C_5$alkylthio; mono- or diphenyl-$C_1$–$C_5$alkylamino; $C_1$–$C_5$alkylthio; cycloalkylthio; unsubstituted or hydroxy- or carboxy-substituted mono- or di-$C_1$–$C_5$alkylamino, the alkyl chain of which may be interrupted by an oxygen atom; mono- or di-$C_3$–$C_5$alkenylamino; unsubstituted or $C_1$–$C_5$alkyl-substituted mono- or dicycloalkylamino; unsubstituted or $C_1$–$C_5$alkyl-, hydroxy- or carboxy-substituted 1-azacycloalkyl; unsubstituted or $C_1$–$C_5$alkyl-substituted morpholino; a radical of formula

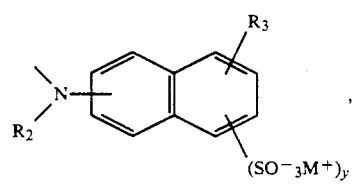

a radical of formula

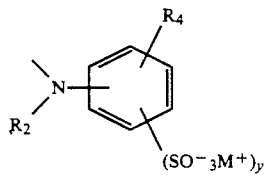

or a radical of formula

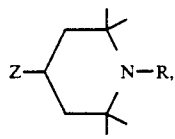

$R_2$ is hydrogen or $C_1$–$C_5$alkyl,
$R_3$ is hydrogen or hydroxy,
$R_4$ is hydrogen; halogen; $C_1$–$C_5$alkyl; $C_1$–$C_5$alkoxy; carboxy; carboxy-$C_1$–$C_5$alkyl; acyl; carbamoyl; or mono- or di-$C_1$–$C_5$-acylamino, M may be the same or different and is hydrogen; alkali metal; alkaline earth metal; ammonia; or an organic ammonio radical of formula $(C_1$–$C_4alkyl)_n(H)_mN^+$,
Z —O—; or —($NR_5$)—,
$R_5$ is hydrogen or $C_1$–$C_5$alkyl,
m is 0 to 3;
n is 1 to 4; and the sum of $m+n=4$,
x is 1 or 2 and
y is 0 or 1;
and, if $R_1$ is a radical of formula (2) or (3) and y is 1, x in formula (1) is 1.

$C_1$–$C_5$Alkyl is typically methyl, ethyl, n-propyl, isopropyl, n-butyl, isobutyl, sec-butyl, tert-butyl, amyl or isoamyl; $C_1$–$C_5$alkoxy is methoxy, ethoxy, isopropoxy, isobutoxy, tert-butoxy or tert-amyloxy; $C_1$–$C_5$alkylthio is methylthio, ethylthio, propylthio or butylthio. Typical examples of mono- and di-$C_1$–$C_5$alkylamino are dimethylamino, diethylamino, dipropylamino or methylethylamino; and typical examples of mono- or di$C_1$–$C_5$-acylamino are formylamino, acetylamino, propionylamino, butyrylamino, diformylamino, diacetylamino, dipropionylamino, dibutyrylamino or formylacetylamino.

Cycloalkyloxyamino, mono- or dicycloalkylamino and cycloalkylthio groups contain 4 to 8, preferably 5 to 7, carbon atoms. Illustrative examples of such groups are cyclobutoxy, cyclopentoxy, cyclohexyloxy, methylcyclohexyloxy, ethylcyclohexyloxy, cycloheptyloxy, cyclooctyloxy, monocyclohexylamino, dicyclohexylamino, cycloheptylthio or cyclohexylthio. The preferred cycloalkoxy group is suitably cyclohexyloxy. The preferred cycloalkylamino group is suitably dicyclohexylamino; and the preferred cycloalkylthio group is suitably cyclohexylthio.

$C_3$–$C_5$Alkenyl, $C_3$–$C_5$alkenyloxy, and mono-or di-$C_3$–$C_5$alkenylamino are radicals that are joined through a saturated carbon atom and are typically butenyl, allyl, butenyloxy, allyloxy, monobutenylamino, monoallylamino, diallylamino or dibutylamino. Preferred radicals are allyl, allyloxy, monoallylamino and diallylamino.

Phenyl-$C_1$–$C_5$alkyl may be phenethyl, phenylpropyl, phenylbutyl or, preferably, benzyl. Phenyl-$C_1$–$C_5$alkoxy, mono- or di(phenyl-$C_1$–$C_5$alkyl)amino and phenyl-$C_1$–$C_5$alkylthio are typically phenylmethoxy, phenylethoxy, phenylpropoxy, monobenzylamino, monophenethylamino, dibenzylamino, diphenethylamino, benzylphenethylamino, benzylthio or phenethylthio. Illustrative examples of carboxy-$C_1$–$C_5$alkyl are carboxymethyl, carboxyethyl, carboxypropyl, carboxyisopropyl, carboxybutyl, carboxyisobutyl, carboxy-sec-butyl, carboxy-tert-butyl, carboxyamyl or carboxyisoamyl.

Halogen radicals in $R_1$ and $R_4$ are fluoro, chloro, bromo, preferably chloro.

In the definition of the radicals R and $R_4$, acyl is preferably formyl, acetyl, propionyl, n-butyryl or benzoyl. 1-Azacycloalkyl is preferably 1-azacycloheptyl, 1-azacyclohexyl or 1-azacyclopentyl.

Typical examples of alkali metals are lithium, sodium or potassium. Sodium is preferred. Typical examples of alkaline earth metals are calcium and magnesium.

A suitable organic ammonio radical of formula $(C_1$–$C_4alkyl)_n(H)_mN^+$ is trimethylammonium or, preferably, triethylammonium.

Mono- or di-$C_1$–$C_5$alkylamino, mono- or di-$C_3$–$C_5$alkenylamino, mono- or di(phenyl-$C_1$–$C_5$alkyl)amino and mono- or dicycloalkylamino may be substituted by alkoxy, hydroxy, carboxy, carboxy-$C_1$-$C_5$alkyl or mono- or di-$C_1$-$C_5$alkylamino. Phenyl-$C_1$-$C_5$alkoxy may be substituted by $C_1$-$C_5$alkyl, halogen or $C_1$-$C_5$alkoxy. $C_1$-$C_5$Alkylthio may be substituted by carboxy or hydroxy. Phenyl-$C_1$-$C_5$alkylthio may be substituted by halogen. 1-Azacycloalkyl may be substituted by $C_1$-$C_3$alkyl, hydroxy or carboxy. Phenyl may be substituted by $C_1$-$C_5$alkyl, carboxy-$C_1$-$C_5$aralkyl or $C_1$-$C_5$alkoxy or halogen. Morpholino may be substituted by one or more than one $C_1$-$C_3$alkyl radical.

Important compounds of formula (1) are those wherein R is hydrogen or $C_1$-$C_5$alkyl.

Further interesting compounds of formula (1) are those wherein $R_1$ is halogen or a radical of formula (2), (3) or (4).

Compounds of particular interest are those of formula

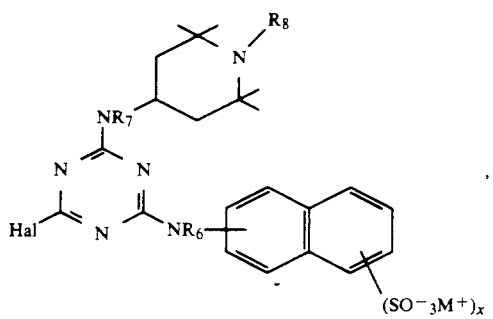
(5)

wherein
$R_6$, $R_7$ and $R_8$ are each independently of one another hydrogen or $C_1$-$C_5$alkyl,
Hal is halogen,
M may be the same or different and is hydrogen or alkali metal, and
x is 1 or 2, or compounds of formula

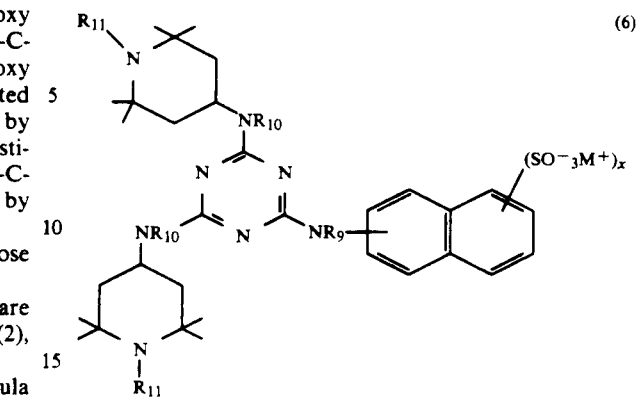
(6)

wherein
$R_9$, $R_{10}$ and $R_{11}$ are each independently of one another hydrogen or $C_1$-$C_5$alkyl,
M may be the same or different and is hydrogen or alkali metal, and
x is 1 or 2.

Further interesting water-soluble triazine derivatives are those of formula

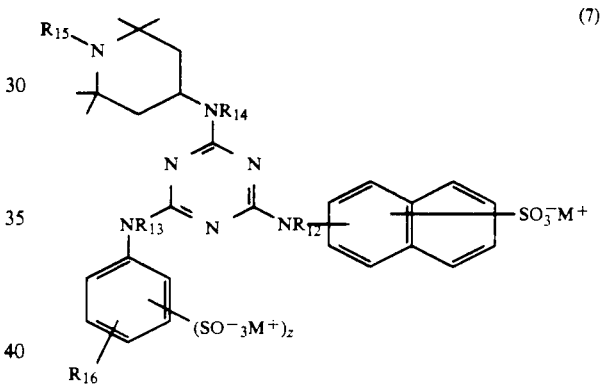
(7)

wherein
$R_{12}$, $R_{13}$, $R_{14}$ and $R_{15}$ are each independently of one another hydrogen or $C_1$-$C_5$alkyl, $R_{16}$ is hydrogen, halogen, $C_1$-$C_5$alkyl, $C_1$-$C_5$alkyl, $C_1$-$C_5$alkoxy, carboxy, carboxy-$C_1$-$C_5$alkyl, mono- or di$C_1$-$C_5$-acylamino,
M may be the same or different and is hydrogen or alkali metal, and
z is 0 or 1.

Other important representatives of the water-soluble triazine compounds are those of formula

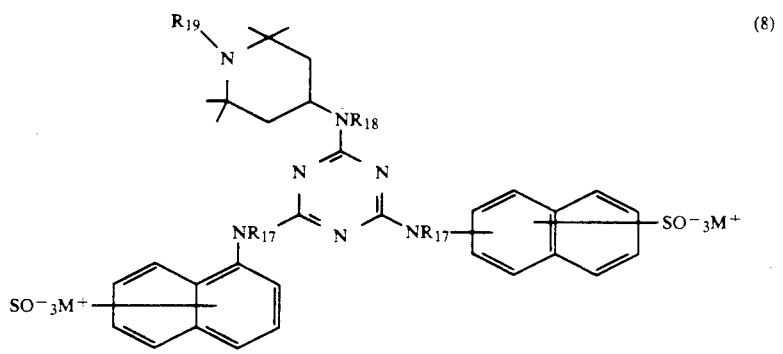
(8)

wherein

R$_{17}$, R$_{18}$ and R$_{19}$ are each independently of one another hydrogen or C$_1$-C$_5$alkyl, and M may be the same or different and is hydrogen or alkali metal.

Further important compounds of formula (1) are those wherein

R$_1$ is a radical of formula $$\begin{array}{c} R_{22} \\ \diagdown \\ N- , \\ \diagup \\ R_{21} \end{array}$$

wherein

R$_{21}$ and R$_{22}$ are each independently of the other hydrogen, C$_1$-C$_5$alkyl, cycloalkyl, unsubstituted or C$_1$-C$_5$alkyl-substituted phenyl, or R$_1$ is 1-azacycloalkyl or morpholino.

The water-soluble triazine derivatives can be prepared in different manner.

The compounds of formula (1) may conveniently be prepared by reacting a compound of formula (9)

[structure: triazine with Hal, Hal, and N-naphthyl-(SO$^-_3$M$^+$)$_x$ with R$_2$, R$_3$]

with 1 mol of the compound of formula (4a)

$$H-Z-\phantom{xx}N-R;$$

or reacting the compound of formula (9) with 1 mol of the compound of formula (2a)

[structure: H-N(R$_2$)-naphthyl with R$_3$ and (SO$^-_3$M$^+$)$_x$]

and 1 mol of the compound of formula (4a); or reacting the compound of formula (9) with 2 mol of the compound (4a) or reacting the compound of formula (9) with 1 mol of a C$_1$-C$_5$alkanolate, C$_3$-C$_5$alkenolate, cycloalkanolate, phenyl-C$_1$-C$_5$alkanolate, phenolate, C$_1$-C$_5$alkylthiolate, cycloalkylthiolate, phenyl-C$_1$-C$_5$alkylthiolate or of a phenylthiolate, of a mono- or di-C$_1$-C$_5$alkylamine, mono- or di-C$_3$-C$_5$alkenylamine, mono- or di(phenyl-C$_1$-C$_5$alkyl)amine, phenylamine, cycloalkylamine, or a 1-azacycloalkyl compound, of a morpholino compound and 1 mol of the compound (4a); or reacting the compound of formula (9) with 1 mol of the compound of formula (3a)

[structure: H-NR$_2$-phenyl with R$_4$ and (SO$^-_3$M$^+$)$_y$]

and 1 mol of the compound of formula (4a), in any order, in which formulae above R is hydrogen, oxyl; hydroxy; C$_1$-C$_5$alkyl; C$_3$-C$_5$alkenyl; C$_1$-C$_5$alkoxy; acyl; or benzyl, R$_2$ is hydrogen or C$_1$-C$_5$alkyl, R$_3$ is hydrogen or hydroxy, R$_4$ is hydrogen; halogen; C$_1$-C$_5$alkyl; C$_1$-C$_5$alkoxy; carboxy; carboxy-C$_1$-C$_5$alkyl; or mono- or diC$_1$-C$_5$-acylamino;

M may be the same or different and is hydrogen, alkali metal, alkaline earth metal, ammonium or an organic ammonio radical of formula (C$_1$-C$_4$alkyl)$_n$(H)$_m$N$^+$, Z is —O— or —(NR$_5$)—, wherein R$_5$ is hydrogen or C$_1$-C$_5$alkyl, Hal is a halogen atom, x is 1 or 2, and y is 0 or 1.

The reaction of the individual reactants with the compound of formula (9) may be carried out in any order.

The compounds of formula (9) are prepared by condensing a 2,4,6-trihalo-s-triazine with an aminonaphthalenesulfonic acid. The triazines, which are preferably used in the form of aqueous dispersions, are commonly known in the art. Cyanuric chloride is especially preferred.

The compounds of formula (9) are useful starting compounds for the synthesis of the novel compounds of formulae (1), (5), (6), (7) and (8).

Compounds of formula (1), wherein R$_1$ is C$_1$-C$_5$alkyl or phenyl, are prepared by reacting 1 mol of a 2,4-dihalo-6-C$_1$-C$_5$alkyl-s-triazine or 2,4-dihalo-6-phenyl-s-triazine in succession with 1 mol of the compound of formula (2a) and 1 mol of the compound of formula (4a).

Water-soluble triazine derivatives of formula (5) are prepared by reacting 1 mol of the compound of formula (9) with 1 mol of the piperidine of formula (4a) to give monopiperidyl-substituted triazine derivatives. In this reaction the reaction temperature is in the range from 0° to 50° C., preferably from 20° to 40° C., and the reaction time is from 1 to 20, preferably from 1 to 4, hours.

The corresponding dipiperidyl-substituted triazines of formula (6) are obtained by reacting the compound of formula (5) with 1 mol of the piperidine of formula (4a).

Dipiperidyl-substituted triazines of formula (6) can also be obtained by reacting 1 mol of the compound of formula (9) with 2 mol of the piperidine of formula (4a). In this reaction the reaction temperature is in the range from 20° to 100° C., preferably from 30° to 80° C.

The compounds of formula (7) are prepared by reacting 1 mol of the compound of formula (9) with 1 mol of the compound of formula (3a) and 1 mol of the compound of formula (4a).

The binaphthyl-substituted triazine derivatives of formula (8) are prepared by reacting 1 mol of the compound of formula (9) in succession with 1 mol of an aminonaphthalenesulfonic acid of formula (2a) and 1 mol of the piperidine of formula (4a).

The water-soluble triazine derivatives of formula (1), wherein

R$_1$ is a radical of formula

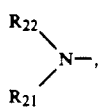

wherein

R$_{21}$ and R$_{22}$ are each independently of the other hydrogen, C$_1$-C$_5$alkyl, cycloalkyl, unsubstituted or C$_1$-C$_5$alkyl-substituted phenyl, or R$_1$ is 1-azacycloalkyl or morpholino, are prepared by reacting a compound of formula (9) with a piperidine of formula (4a) and the corresponding N-alkyl or aminophenyl compound of formula

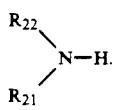

The order in which the reactions of the piperidine of formula (4a) and the N-alkyl compound depends on the reactivity of the respective compounds. The normal procedure is to carry out reaction with that compound which has the lower reactivity.

The hydrohalic acid formed in the condensation reactions can be neutralised by the final product itself or by addition of a further base, conveniently aqueous ammonia, an alkali metal hydroxide, an alkali metal carbonate or hydrogen carbonate, or an organic base such as triethylamine.

The compounds of formulae (1) to (5) and (8) are preferably used as sodium salts by dissolving them in e.g. the equivalent amount of aqueous sodium hydroxide.

The novel triazine derivatives are suitable for enhancing the photochemical and thermal stability of undyed and dyed polyamide fibre materials. The invention accordingly further relates to a process for the photochemical and thermal stabilisation of polyamide fibre materials, which process comprises treating dyed or undyed polyamide fibre materials with a water-soluble triazine derivative of formula

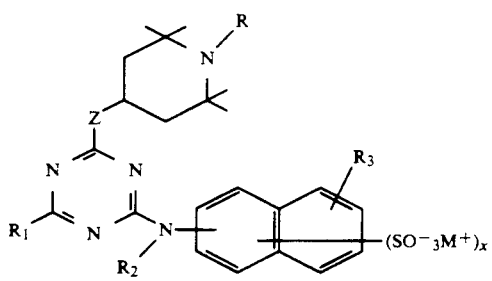

wherein

R is hydrogen, oxyl; hydroxy; C$_1$-C$_5$alkyl; C$_3$-C$_5$alkenyl; C$_1$-C$_5$alkoxy; acyl; or benzyl, R$_1$ is halogen; C$_1$-C$_5$alkyl; amino; C$_1$-C$_5$alkoxy; C$_3$-C$_5$alkenyloxy; cycloalkoxy; unsubstituted phenoxy or phenoxy which is substituted in the phenyl moiety by halogen, C$_1$-C$_5$alkyl, C$_1$-C$_5$alkoxy, carboxy, carboxy-C$_1$-C$_5$alkyl, carbamoyl, mono- or diC$_1$-C$_5$acylamino or acyl; phenyl; phenyl-C$_1$-C$_5$alkyl; phenylthio; phenyl-C$_1$-C$_5$alkylthio; mono- or diphenyl-C$_1$-C$_5$alkylamino; C$_1$-C$_5$alkylthio; cycloalkylthio; unsubstituted or hydroxy- or carboxy-substituted mono- or di-C$_1$-C$_5$alkylamino, the alkyl chain of which may be interrupted by an oxygen atom; mono- or di-C$_3$-C$_5$alkenylamino; unsubstituted or C$_1$-C$_5$alkyl-substituted mono- or dicycloalkylamino; unsubstituted or C$_1$-C$_5$alkyl-, hydroxy- or carboxy-substituted 1-azacycloalkyl; unsubstituted or C$_1$-C$_5$alkyl-substituted morpholino; a radical of formula

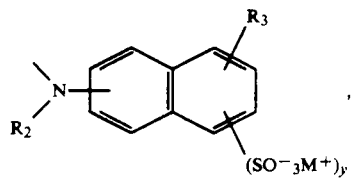

a radical of formula

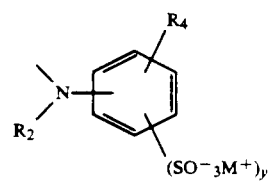

or a radical of formula

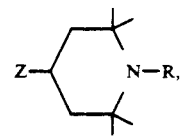

R$_2$ is hydrogen or C$_1$-C$_5$alkyl,

R$_3$ is hydrogen or hydroxy,

R$_4$ is hydrogen; halogen; C$_1$-C$_5$alkyl; C$_1$-C$_5$alkoxy; carboxy; carboxy-C$_1$-C$_5$alkyl; acyl; carbamoyl; or mono- or diC$_1$-C$_5$-acylamino, M may be the same or different and is hydrogen; alkali metal; alkaline earth metal; ammonia; or an organic ammonio radical of formula (C$_1$-C$_4$alkyl)$_n$(H)$_m$N$^+$, Z —O—; or —(NR$_5$)—, R$_5$ is hydrogen or C$_1$-C$_5$alkyl, m is 0 to 3;

n is 1 to 4; and the sum of m+n=4, x is 1 or 2 and y is 0 or 1;

and, if R$_1$ is a radical of formula (2) or (3) and y is 1, x in formula (1) is 1.

The novel compounds are representatives of the sterically hindered amines (HALS stabilisers) and they can be applied to the polyamide fibre materials from conventional liquors by standard methods.

In the practice of this invention it is preferred to apply these compounds from an aqueous bath that contains the compounds in a concentration of 0.005 to 10%, preferably 0.05 to 2%, by weight. The compounds are preferably added to the dyebath. Application can be made before, after or during dyeing by an exhaust or continuous process. Application during dyeing is preferred.

In the exhaust process the liquor ratio can vary over a wide range, typically from 1:5 to 1:300, preferably from 1:10 to 1:50. The process is conveniently carried out in the temperature range from 30° to 120° C., preferably from 50° to 98° C.

In the continuous process the liquor is conveniently applied to a pick-up of 30–400% by weight, preferably of 75–250% by weight. The dyes and novel compounds are fixed on the fibre material by subjecting the material to a heat treatment. The fixation process can also be carried out by the cold pad-batch method.

The heat treatment is preferably carried out by steaming in a steamer with steam or superheated steam in the temperature range from 98°–105° C. for conveniently 1 to 7, preferably for 1 to 5, minutes. The fixation of the dyes and the compounds of formula (1) by the cold pad-batch method can be effected by storing the impregnated and preferably rolled up goods at room temperature (15°–30° C.), conveniently for 3 to 24 hours, the cold batching time depending naturally on the type of dye used.

When the dyeing process and fixation are complete, the dyeings are washed off and dried in conventional manner.

The polyamide fibre materials obtained, and the dyeings produced thereon, by the process of this invention have good photochemical and thermal stability.

The dyeings that are photochemically and thermally stabilised in the practice of this invention are those produced with acid or metal complex dyes, typically 1:2 chromium, 1:2 cobalt or copper complex dyes, and also with disperse and reactive dyes.

Examples of such dyes are listed in the Colour Index, 3rd Edition 1971, Volume 4.

Polyamide fibre material will be understood as meaning in the context of this invention synthetic polyamide, including polyamide 6, polyamide 66 and also polyamide 12, as well as modified polyamide, e.g. basic dyeable polyamide. In addition to pure polyamide fibres, polyurethane/polyamide blends, for example tricot material made from polyamide/polyurethane in the ratio 70:30, are also suitable. Polypropylene/polyamide blends can also suitably be used. Basically the pure polyamide material or blends thereof may be in any form of presentation, including fibres, yarn, woven fabrics, knitted fabrics, nonwovens or pile material.

The novel water-soluble compounds are especially suitable for the treatment of polyamide fibre material that is exposed to the influence of light and heat, for example car upholstery or carpets.

The invention is illustrated by the following Examples in which parts and percentages are by weight.

Preparation of the compounds of formula (1)

EXAMPLE 1

With rapid stirring, 7.8 g of 4-amino-2,2,6,6-tetramethylpiperidine are added dropwise to a neutral suspension of 19.7 g of the sodium salt of 1-N-(2,4-dichloro-6-s-triazinyl)aminonaphthalene-6-sulfonic acid in 100 ml of distilled water. The reaction mixture is then stirred for hours at 35° C. After cooling to room temperature, the reaction mixture is filtered and the filter product is washed with distilled water and dried at 50° C. under vacuum, giving 11.5 g of a white powder of formula

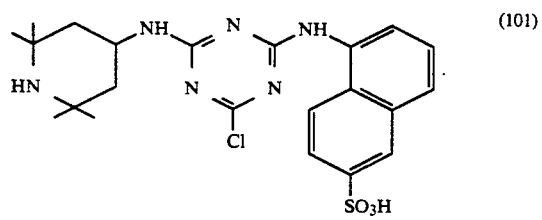

The compound has $\lambda_{max}=280$ nm (in water).

EXAMPLE 2

With stirring, 2.3 g of aniline are added dropwise at room temperature over 5 minutes to a neutral suspension of 16.4 g of the monocondensate of cyanuric chloride and the sodium salt of 2-aminonaphthalene-6-sulfonic acid (active substance content 60%) in 100 ml of distilled water. The pH of the reaction mixture is kept at 6–7 by the dropwise addition of concentrated aqueous sodium hydroxide. The condensation is complete after stirring for 2 hours. After dilution with 50 ml of distilled water and the rapid addition of 3.9 g of 4-amino-2,2,6,6-tetramethylpiperidine, the batch is stirred for 16 hours at 80° C. The reaction mixture is cooled to room temperature and the precipitate is filtered with suction, washed with distilled water and dried at 65° C. under vacuum, giving 13.8 g of a colourless compound of formula

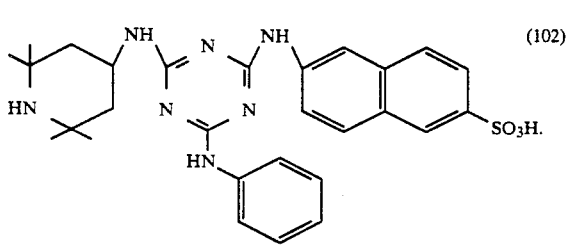

The compound has $\lambda_{max}=299$ nm (in borax buffer).

EXAMPLE 3

1.9 g of aniline are added at room temperature to a neutral suspension of 14.8 g of the monocondensate of cyanuric chloride and the disodium salt of 3-aminonaphthalene-1,5-disulfonic acid (active substance content 67%) in 100 ml of distilled water. With stirring, the reaction mixture is warmed to 40° C. and the pH is kept at 6–7 by the dropwise addition of concentrated aqueous sodium hydroxide. When the condensation is complete (1 hour), 3.1 g of 4-amino-2,2,6,6-tetramethylpiperidine are added and the reaction mixture is heated for 16 hours to 75° C. The reaction mixture is then cooled to room temperature and the product is salted out with 12 g of sodium chloride. The precipitate is filtered with suction, washed with a 10% solution of sodium chloride and dried at 65° C. under vacuum, giving 18.2 g of a powder of formula

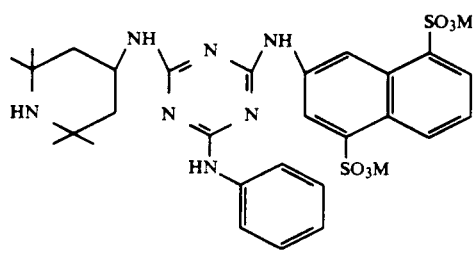

M = H, Na

The compound has $\lambda_{max}=337$ nm (in water).

EXAMPLE 4

A solution of 3.7 g of cyanuric chloride in 20 ml of acetone is poured on to 100 ml of ice-water and then 4.5 g of 1-aminonaphthalene-6-sulfonic acid are added. The reaction mixture is stirred at 0°–5° C. and the pH is kept at 2.5–3 by the dropwise addition of concentrated aqueous sodium hydroxide. After 1 hour the mixture is warmed to room temperature and another 4.5 g of 1-aminonaphthalene-6-sulfonic acid are added. The pH of the reaction mixture is kept at 6–7 by the further dropwise addition of concentrated aqueous sodium hydroxide and the batch is stirred for 2 hours. Finally, 3.75 g of 4-amino-2,2,6,6-tetramethylpiperidine are added rapidly to the reaction mixture, which is heated for 16 hours to 70° C. The precipitate is filtered with suction at room temperature, washed with acetone and water and dried at 50° C. under vacuum, giving 10.3 g of a white powder of formula

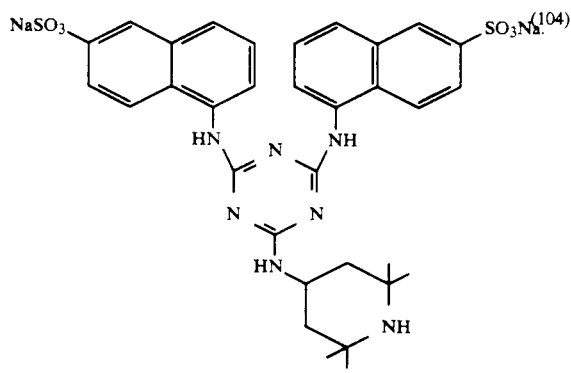

The compound has $\lambda_{max}=292$ nm (in borax buffer).

EXAMPLE 5

9.4 g 4-amino-2,2,6,6-tetramethylpiperidine are added rapidly at room temperature to a neutral suspension of 13.1 g of the monocondensate of cyanuric chloride and the sodium salt of 2-aminonaphthalene-6-sulfonic acid (active substance content 60%) in 100 ml of distilled water, and the mixture is stirred for 18 hours at 80° C. After cooling to room temperature, the reaction mixture is filtered and the filter product is washed with water and dried at 65° C. under vacuum, giving 13.3 g of a colourless powder of formula

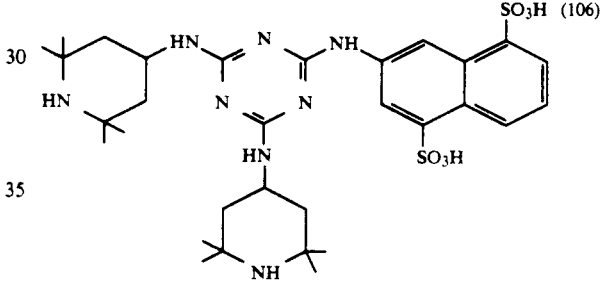

The compound has $\lambda_{max}=300$ nm (in borax buffer).

EXAMPLE 6

6.25 g of 4-amino-2,2,6,6-tetramethylpiperidine are added at room temperature to a neutral suspension of 14.8 g of the monocondensate of cyanuric chloride and the disodium salt of 3-aminonaphthalene-1,5-disulfonic acid (active substance content 67%) in 100 ml of distilled water, and the mixture is stirred for 48 hours at 75° C. After cooling to room temperature, the reaction mixture is filtered and the filter product is washed with water and dried at 65° C. under vacuum, giving 13.6 g of a white powder of formula

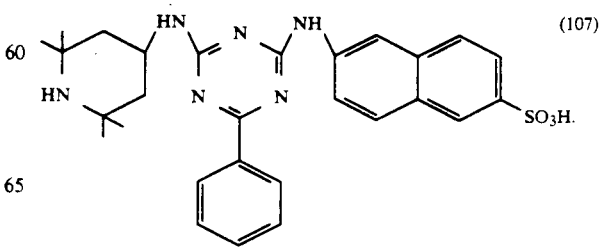

The compound has $\lambda_{max}=337$ nm (in water).

EXAMPLE 7

A solution of 6.3 g of 2-phenyl-4,6-dichloro-s-triazine in 15 ml of acetone is charged into 50 ml of distilled water. Then 6.9 g of the sodium salt of 2-amino-naphthalene-6-sulfonic acid are added with rapid stirring. The temperature is raised to 40° C. and the pH of the reaction mixture is kept at 6 by the dropwise addition of concentrated aqueous sodium hydroxide. After 4 hours the condensation is complete, and then 4.4 g of 4-amino-2,2,6,6-tetramethylpiperidine are added rapidly to the mixture. The reaction mixture is heated for 16 hours to 75° C. After cooling to room temperature, the precipitate is filtered with suction, washed with water and dried at 65° C. under vacuum, giving 11.9 g of a colourless powder of formula The compound has $\lambda_{max}=304$ nm (in borax buffer).

EXAMPLE 8

With rapid stirring, a solution of 8.3 g of the disodium salt of 3-amino-naphthalene-1,5-disulfonic acid in 50 ml of distilled water is added to a suspension of 5.4 g of 2-phenyl-4,6-dichloro-s-triazine in 15 ml of acetone/50 ml of distilled water. The reaction mixture is warmed for 4 hours to 35° C. and the pH of the reaction mixture is kept at 5-6 by the dropwise addition of concentrated aqueous sodium hydroxide. Then 3.75 g of 4-amino-2,2,6,6-tetramethylpiperidine are added rapidly to the mixture. The reaction mixture is stirred for 16 hours at 75° C. After cooling to room temperature, the reaction mixture is filtered and the filter product is washed with a small amount of water and acetone and dried under vacuum at 65° C., giving 12.3 g of a powder of formula

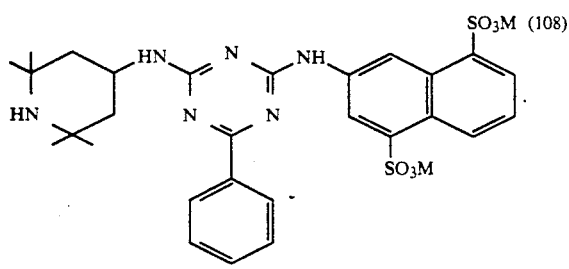

M = Na, H

The compound has $\lambda_{max}$ (as shoulder) = 340 nm (in water).

EXAMPLE 9

With stirring, 2.18 g of morpholine are added dropwise over 5 minutes at room temperature to a neutral suspension of 16.4 g of the monocondensate of cyanuric chloride and the sodium salt of 2-aminonaphthalene-6-sulfonic acid (active substance content 60%) in 100 ml of distilled water. The pH of the reaction mixture is kept at 6-7 by the dropwise addition of concentrated aqueous sodium hydroxide. The reaction mixture is stirred for 2 hours at room temperature and for 1.5 hours at 40° C. Then 3.9 g of 4-amino-2,2,6,6-tetramethylpiperidine are added rapidly to the reaction mixture. The temperature is raised to 80° C. and the mixture is stirred for 16 hours. After cooling to room temperature, the precipitate is filtered with suction, washed with water and dried at 65° C. under vacuum, giving 11.9 g of a colourless compound of formula

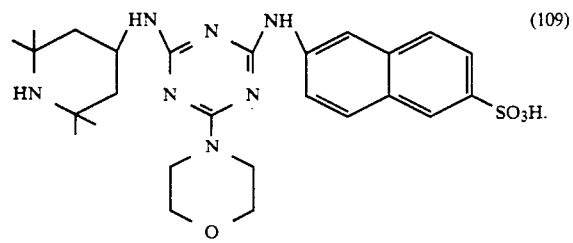

The compound has $\lambda_{max}=300$ nm (in borax buffer).

EXAMPLE 10

The procedure of Example 9 is repeated, using 2.76 g of thiophenol instead of 2.18 g of morpholine, to give 11.9 g of a colourless product of formula

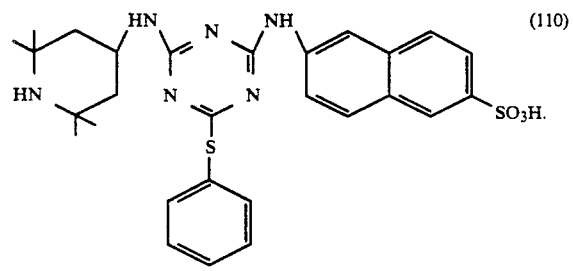

The compound has $\lambda_{max}=304$ nm (in borax buffer).

EXAMPLE 11

3.77 g of 4-amino-2,2,6,6-tetramethylpiperidine are added rapidly to a neutral suspension of 15.8 g of the monocondensate (active substance content 60%) of cyanuric chloride and 2-aminonaphthalene-6-sulfonic acid in 100 ml of distilled water, and the mixture is warmed for 2 hours to 40° C. After cooling to room temperature, the precipitate is isolated by filtration, washed with distilled water, and dried at 40° C. under vacuum, giving 12.35 g of a white powder of formula

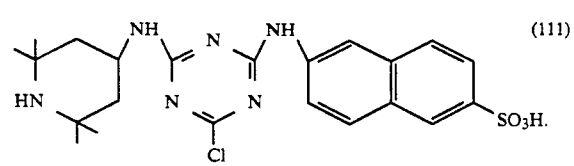

The compound has $\lambda_{max}=300$ nm (in borax buffer).

EXAMPLE 12

2.34 g of 4-amino-2,2,6,6-tetramethylpiperidine are added rapidly at room temperature to a neutral suspension of 11.05 g of the monocondensate (active substance content 67%) of cyanuric chloride and 3-aminonaphthalene-1,5-disulfonic acid in 100 ml of distilled water. The reaction solution is then warmed for 1 hour to 40° C. After cooling to room temperature, the mixture is poured into 500 ml of acetone and the precipitate is filtered with suction, washed with acetone and dried at 40° C. under vacuum, giving 10.2 g of a crystalline powder of formula

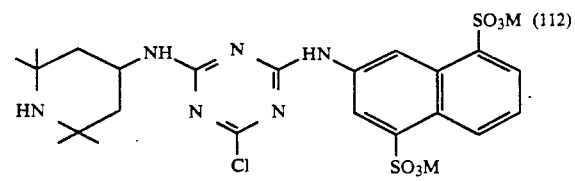

M = H, Na

The compound has $\lambda_{max}$ (as shoulder) = 335 nm (in water).

EXAMPLE 13

The procedure of Example 3 is repeated, using 1.74 g of morpholine instead of 1.9 g of aniline, to give a compound of formula

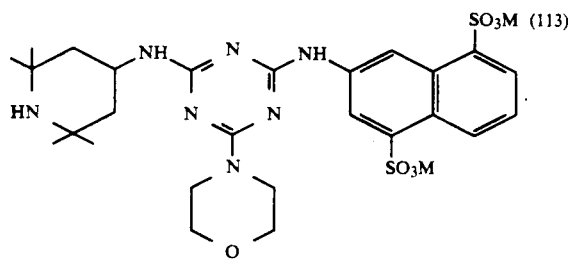

M = H, Na

The compound has $\lambda_{max} = 340$ nm (in water).

EXAMPLE 14

The procedure of Example 3 is repeated, using 2.2 g of thiophenol instead of 1.9 g of aniline, to give a compound of formula

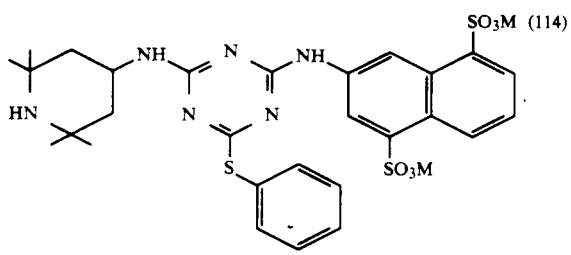

M = H, Na

The compound has $\lambda_{max} = 340$ nm (as shoulder) in water.

Application Examples

EXAMPLE 15

14 samples (10 g each) of a polyamide 6 knitted fabric are prepared and blank dyed (i.e. treated without dye: liquors 1,3,5,7,9,11 and 13) and dyed (liquors 2,4,6,8,10,12 and 14) in a laboratory dyeing machine, e.g. an ® AHIBA machine, at a liquor ratio of 1:25.

The 14 liquors so prepared each contain 0.5 g/l of monosodium phosphate, 1.5 g/l of disodium phosphate (=pH 7) and a dyeing auxiliary (® Albegal SW). To liquors 2,4,6,8, 10,12 and 14 are added the following dyes in dissolved form:

0.04% of the mixture comprising 81 parts of the compound of formula

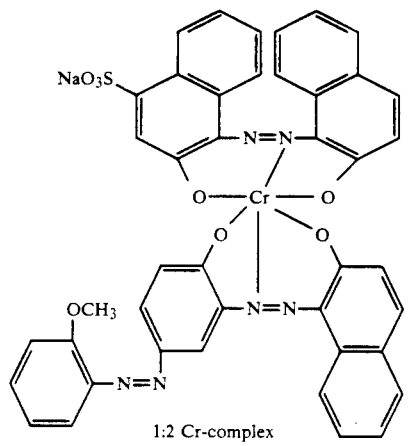

1:2 Cr-complex and 12 parts of the compound of formula

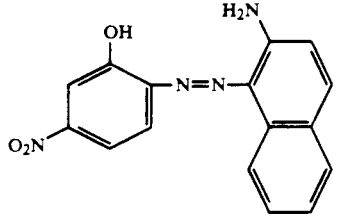

1:2 Co-complex
(remainder of 7 parts comprises salts and surfactants)
and 0.002% of the dye of formula

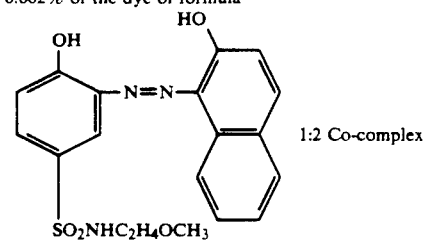

1:2 Co-complex

Liquors 3 and 4 additionally contain 0.1% of the sodium salt of the compound of formula (101).

Liquors 5 and 6 each contain 0.1% of the sodium salt of the compound of formula (102).

Liquors 7 and 8 each contain 0.1% of the sodium salt of the compound of formula (104).

Liquors 9 and 10 each contain 0.1% of the sodium salt of the compound of formula (105).

Liquors 11 and 12 each contain 0.1% of the sodium salt of the compound of formula (110).

Liquors 13 and 14 each contain 0.1% of the sodium salt of the compound of formula (109).

The prepared textile material is put at 40° C. into the liquors, left for 10 minutes at this temperature and heated at 2° C./minute to 95° C. After a treatment time of 20 minutes, 2% of acetic acid (80%) is added and treatment is continued for a further 20 minutes. Finally, the liquor is cooled to 60° C. and the samples are washed off, centrifuged and dried.

The treated samples are irradiated for 216 hours according to DIN 75.202 (=FAKRA). Tear strength and stretch are determined according to SN 198.461. The lightfastness of the dyeings is also measured according to DIN 75.202. The results are reported in Table 1.

TABLE I

| Liquor/Compound | | Tear strength/ stretch [%] after 216 h FAKRA | Lightfastness After 44 H FAKRA[3] |
|---|---|---|---|
| liquor 1: | none | 2.7/11.9 | —[1] |
| liquor 2: | none | —[1] | <<1H[2] |
| liquor 3 | + compound (101) | 51.9/48.2 | —[1] |
| liquor 4 | | —[1] | 1-2 |
| liquor 5: | + compound (102) | 59.0/53.9 | —[1] |
| liquor 6: | | —[1] | 2-3 |
| liquor 7: | + compound (104) | 53.5/52.1 | —[1] |
| liquor 8: | | —[1] | 2 |
| liquor 9: | + compound (105) | 40.4/40.9 | —[1] |
| liquor 10: | | —[1] | 2 |
| liquor 11: | + compound (110) | 54.5/50.4 | —[1] |
| liquor 12: | | —[1] | 2-3 |
| liquor 13: | + compound (109) | 47.4/46.2 | —[1] |

TABLE I-continued

| Liquor/Compound | Tear strength/ stretch [%] after 216 h FAKRA | Light-fastness After 44 H FAKRA[3] |
|---|---|---|
| liquor 14: | —[1] | 2–3 |

[1] not tested
[2] sample no longer tear-resistant: faded
[3] corresponds to 2 exposure cycles The results in table I demonstrate that the compounds of the present invention effect an evident improvement of the photochemical stability of the polyamide fibre and dyeings.

What is claimed is:

1. A water-soluble compound of formula

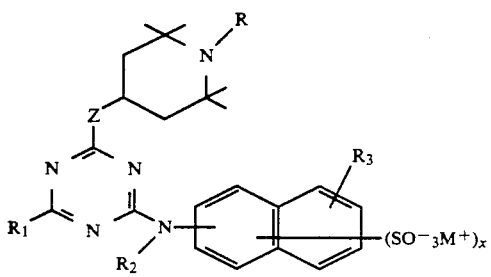

(1)

wherein

R is hydrogen, oxyl; hydroxy; $C_1-C_5$alkyl; $C_3-C_5$alkenyl; $C_1-C_5$alkoxy; acyl; or benzyl, $R_1$ is halogen; $C_1-C_5$alkyl; amino; $C_1-C_5$alkoxy; $C_3-C_5$alkenyloxy; cycloalkoxy; unsubstituted phenoxy or phenoxy which is substituted in the phenyl moiety by halogen, $C_1-C_5$alkyl, $C_1-C_5$alkoxy, carboxy, carboxy-$C_1-C_5$alkyl, carbamoyl, mono- or di-$C_1-C_5$-acylamino or acyl; phenyl; phenyl-$C_1-C_5$alkyl; phenylthio; phenyl-$C_1-C_5$alkylthio; mono- or diphenyl-$C_1-C_5$alkylamino; $C_1-C_5$alkylthio; cycloalkylthio; unsubstituted or hydroxy- or carboxy-substituted mono- or di-$C_1-C_5$alkylamino, wherein the alkyl groups may be interrupted by an oxygen atom; mono- or di-$C_3-C_5$alkenylamino; unsubstituted or $C_1-C_5$alkyl-substituted mono- or dicycloalkylamino; unsubstituted or $C_1-C_5$alkyl-, hydroxy- or carboxy-substituted 1-azacyclohexyl; unsubstituted or $C_1-C_5$alkyl-substituted morpholino; a radical of formula

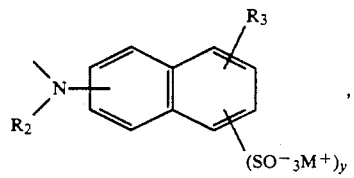

(2)

a radical of formula

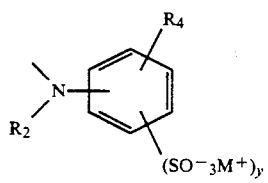

(3)

or a radical of formula

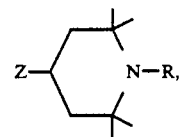

(4)

$R_2$ is hydrogen or $C_1-C_5$alkyl, $R_3$ is hydrogen or hydroxy, $R_4$ is hydrogen; halogen; $C_1-C_5$alkyl; $C_1-C_5$alkoxy; carboxy; carboxy-$C_1-C_5$alkyl; acyl; carbamoyl; or mono- or di-$C_1-C_5$-acylamino, M may be the same or different and is hydrogen; alkali metal; alkaline earth metal; ammonia; or an organic ammonio radical of formula $(C_1-C_4alkyl)_n(H)_mN^+$, Z —O—; or —($NR_5$)—, $R_5$ is hydrogen or $C_1-C_5$alkyl, m is 0 to 3;

n is 1 to 4; and the sum of m+n=4, x is 1 or 2 and y is 0 or 1;

and, if $R_1$ is a radical of formula (2) or (3) and y is 1, x in formula (1) is 1.

2. A compound according to claim 1, wherein R is hydrogen or $C_1-C_5$alkyl.

3. A compound according to claim 1, wherein $R_1$ is halogen or a radical of formula (2), (3) or (4).

4. A compound according to claim 1 of formula

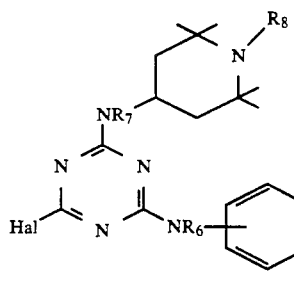

(5)

wherein $R_6$, $R_7$ and $R_8$ are each independently of one another hydrogen or $C_1-C_5$alkyl, Hal is halogen, M may be the same or different and is hydrogen or alkali metal, and x is 1 or 2.

5. A compound according to claim 1 of formula

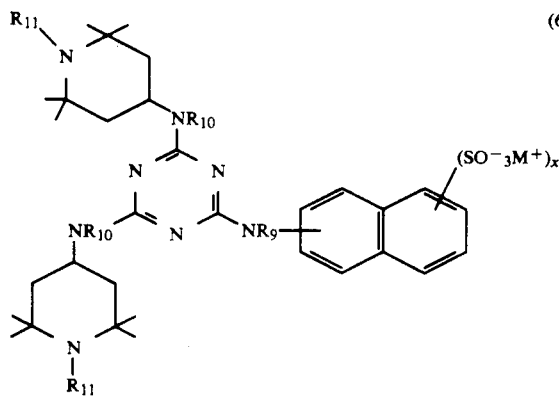

wherein
R$_9$, R$_{10}$ and R$_{11}$ are each independently of one another hydrogen or C$_1$-C$_5$alkyl,
M may be the same or different and is hydrogen or alkali metal, and
x is 1 or 2.

6. A compound according to claim 1 of formula

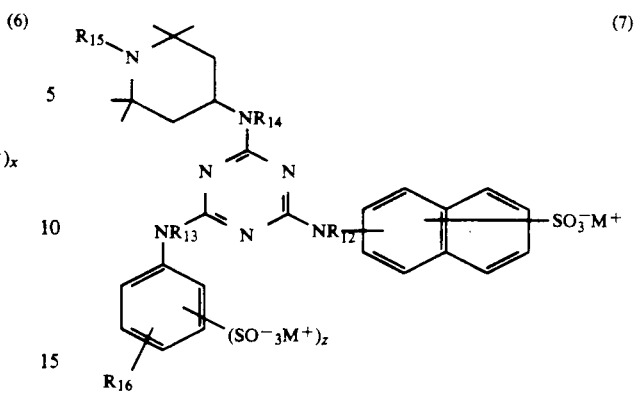

wherein
R$_{12}$, R$_{13}$, R$_{14}$ and R$_{15}$ are each independently of one another hydrogen or C$_1$-C$_5$alkyl,
R$_{16}$ is hydrogen, halogen, C$_1$-C$_5$alkyl, C$_1$-C$_5$alkoxy, carboxy, carboxy-C$_1$-C$_5$alkyl, mono- or di-C$_1$-C$_5$-acylamino,
M may be the same or different and is hydrogen or alkali metal, and
z is 0 or 1.

7. A compound according to claim 1 of formula

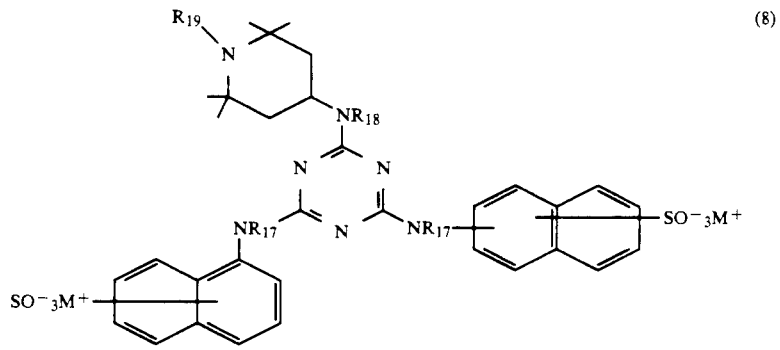

wherein
R$_{17}$, R$_{18}$ and R$_{19}$ are each independently of one another hydrogen or C$_1$-C$_5$alkyl, and each
M is independently hydrogen or alkali metal.

8. A compound according to claim 1, wherein in formula (1)
R$_1$ is a radical of formula

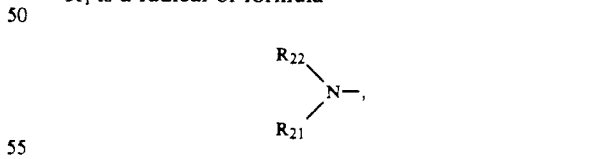

wherein
R$_{21}$ and R$_{22}$ are each independently of the other hydrogen, C$_1$-C$_5$alkyl, cycloalkyl, unsubstituted or C$_1$-C$_5$alkyl-substituted phenyl, or
R$_1$ is 1-azacyclohexyl or morpholino.

* * * * *